United States Patent [19]

Treybig et al.

[11] Patent Number: 4,880,934
[45] Date of Patent: Nov. 14, 1989

[54] PREPARATION OF HYDROXYALKYLPIPERAZINONES BY REACTING A 2,3-DIHYDROXY-1,4-DIOXANE WITH A HYDROALKYLDIAMINE

[75] Inventors: Duane S. Treybig; John M. Motes, both of Lake Jackson, Tex.

[73] Assignee: The Dow Chemical Company, Midland, Mich.

[21] Appl. No.: 279,906

[22] Filed: Dec. 5, 1988

Related U.S. Application Data

[62] Division of Ser. No. 85,428, Aug. 13, 1987, Pat. No. 4,814,443.

[51] Int. Cl.$^4$ ............................................. C07D 241/08
[52] U.S. Cl. ..................................... 544/384; 540/492
[58] Field of Search ........................................... 544/384

[56] References Cited

U.S. PATENT DOCUMENTS 4,767,860  8/1988  Dunmore et al. .................. 544/384

Primary Examiner—Glennon H. Hollrah
Assistant Examiner—James H. Turnipseed
Attorney, Agent, or Firm—A. Cooper Ancona

[57] ABSTRACT

A process for the preparation of 4-(2-hydroxyalkyl)-2-piperazinones and their substituted derivatives comprising reacting an N-hydroxyalkylalkylenediamine, e.g. 2-[(2-aminoethyl)amino]ethanol, or a hydrocarbyl substituted derivative thereof with an $\alpha,\beta$-dicarbonyl compound, e.g. glyoxal, an alkyl-substituted derivative of glyoxal or a glyoxal equivalent. Certain hexahydro-4-(hydroxyalkyl)-2H-1,4-diazepin-2-ones have been made which are new compounds.

16 Claims, No Drawings

PREPARATION OF HYDROXYALKYLPIPERAZINONES BY REACTING A 2,3-DIHYDROXY-1,4-DIOXANE WITH A HYDROALKYLDIAMINE

This is a division of application Ser. No. 085,428, filed Aug. 13, 1987, now Pat. No. 4,814,443.

BACKGROUND OF THE INVENTION

The present invention pertains to 4-(2-hydroxyalkyl)-2-piperazinones, hexahydro-4-(hydroxyalkyl)-2H-1,4-diazepin-2-ones and their substituted derivatives. The 4-(2-hydroxyalkyl)-2-piperazinones have been prepared by reacting the appropriate 2-piperazinone or 3-substituted alkyl- or aryl-2-piperazinones with ethylene oxide or ethylene chlorohydrin. This early research is disclosed in *Chimie Therapeutique,* May-June, 1969, No. 3, pp. 167–173 and in U.S. Pat. No. 2,633,467. The substituted 4-(2-hydroxyethyl)-2-piperazinones include compounds such as 4-(2-hydroxyethyl)-3-methyl-2-piperazinone and 4-(2-hydroxyethyl)-3,3-methyl-2-piperazinone the like alkyl and aryl substituted 2-piperazinones.

The present invention provides a more economical route for the preparation of the subject compounds in that it is not necessary to make the piperazinone starting reactant of the known art.

SUMMARY OF THE INVENTION

A new method has been discovered for the preparation of 4-(2-hydroxyalkyl)-2-piperazinones and their substituted derivatives. These are prepared by reacting an N-hydroxyalkylalkylenediamine or a hydrocarbyl substituted derivative thereof with an $\alpha,\beta$-dicarbonyl compound such as glyoxal, an alkyl-substituted derivative of glyoxal or a glyoxal equivalent. The term "hydrocarbyl" employed herein means any alkyl, cycloalkyl, aromatic, aralkyl or alkaryl radical.

The reaction of the above $\alpha,\beta$-dicarbonyl-type reactants with certain of the N-hydroxyalkylalkylenediamines or their hydrocarbyl substituted derivatives has produced a new class of cyclic amides. These amides are prepared by reacting certain N-hydroxyalkyl-propanediamines or their substituted derivatives with the $\alpha,\beta$-dicarbonyl compounds. The new amides are hexahydro-4-(2-hydroxyalkyl)-2H-1,4-diazepin-2-ones.

The hydroxyalkylpiperazinones and hexahydro(hydroxyalkyl)diazepinones made by the process of the invention are useful as acid corrosion inhibitors. Some of the products of the invention are useful as adhesion promoters. The use of certain of the products of the invention as regenerative solvents for the desulfurization of flue gas is described and claimed in a separate co-filed application entitled "Sulfur Dioxide Removal from Gas Streams Using Hydroxyalkyl Substituted Piperazinones", identified as Docket Number C-32,814.

DETAILED DESCRIPTION OF THE INVENTION

Suitable hydroxyalkylalkylenediamines to be reacted with glyoxal or its derivatives include those having the formula

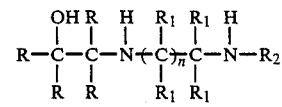

wherein R is hydrogen or an alkyl group of 1 or 2 carbon atoms, $R_1$ is hydrogen, an alkyl group of 1–6 carbon atoms or an aryl or an aralkyl group having from 6 to 12 carbon atoms and $R_2$ is hydrogen, an alkyl or hydroxyalkyl group of 1–6 carbon atoms or an aryl or an aralkyl group having from 6 to 12 carbon atoms and n is 1 or 2.

Especially suitable hydroxyalkylalkylenediamines for the reaction include 2-[(2-aminoethyl)-amino]ethanol-(AEEA), 2-[(3-aminopropyl)amino]ethanol, 2-[(2-amino-1-methylethyl)amino]ethanol, 2-[(2-aminopropyl)aminoethanol(APAE), 2-[(2-amino-1,1-dimethylethyl)amino]ethanol, 2-[(2-amino-2-methylpropyl)amino]-ethanol, 2-[[2-(methylamino)ethyl]amino]ethanol, 2-[[2-(ethylamino)ethyl]amino]ethanol, 2-[(2-amino-1-phenylethyl)amino]ethanol, 2-[[2-(phenylamino)ethyl]amino]-ethanol, 2,2'-(1,2-ethanediyldiimino)bisethanol, 1-[(2-aminoethyl)amino]-2-propanol, 1-[(3-aminopropyl)amino]-2-propanol, 1-[(2-aminopropyl)amino]-2-propanol, 1-[(2-aminoethyl)amino]-2-butanol, and the like or mixtures thereof.

Suitable $\alpha,\beta$-dicarbonyl compounds are those having the formula

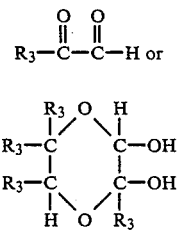

wherein R and $R_1$ have been previously defined and $R_3$ is hydrogen or an alkyl group having from 1–4 carbon atoms.

The preferred $\alpha,\beta$-dicarbonyl compounds are glyoxal, pyruvaldehyde (methyl glyoxal), 1,2-butanedione, 1,2-pentanedione, and the like and mixtures thereof. Other compounds which are equivalent to glyoxal or its derivatives are glyoxal dihydrate, dilute aqueous solutions of glyoxal, e.g. 40%, glyoxal hydrogen sulfite, alkali metal di-salts of 1,2-dihydroxy-1,2-ethanedisulfonic acid and 2,3-dihydroxy-1,4-dioxane and its alkyl derivatives. The hydrogen sulfite derivative of glyoxal when treated with a base liberates glyoxal. The preparation of the dihydroxy dioxane is described in *Synthesis* by M. C. Venuti, 1982, Thieme-Stratton Inc., New York, p. 62, the same being incorporated herein by reference.

The 4-(2-hydroxyalkyl)-2-piperazinones which can be made according to the process of the invention include those of the formula:

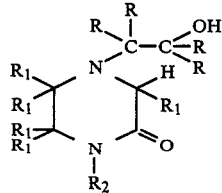

wherein R is hydrogen or an alkyl group having 1 or 2 carbon atoms, $R_1$ is hydrogen, an alkyl group having 1 to 6 carbon atoms or an aryl or an aralkyl group having from 6 to 12 carbon atoms and $R_2$ is hydrogen, an alkyl or hydroxyalkyl group having from 1 to 6 carbon atoms or an aryl or aralkyl group having from 6 to 12 carbon atoms.

The 4-(2-hydroxyalkyl)-2-piperazinones include 4-(2-hydroxyethyl)-2-piperazinone, 4-(2-hydroxyethyl)-1-methyl-2-piperazinone, 4-(2-hydroxyethyl)-3-methyl-2-piperazinone, 4-(2-hydroxyethyl)-5-methyl-2-piperazinone, 4-(2-hydroxyethyl)-6-methyl-2-piperazinone, 3-ethyl-4-(2-hydroxyethyl)-2-piperazinone, 6-ethyl-4-(2-hydroxyethyl)-2-piperazinone, 4-(2-hydroxyethyl)-5,6-dimethyl-2-piperazinone, 1-ethyl-4-(2-hydroxyethyl)-2-piperazinone, 4-(2-hydroxyethyl)-3-phenyl-2-piperazinone, 1,4-bis(2-hydroxyethyl)-2-piperazinone, 4-(2-hydroxypropyl)-2-piperazinone, 4-(2-hydroxybutyl)-2-piperazinone, and 4-(2-hydroxypropyl)-6-methyl-2-piperazinone.

Hexahydro-4-(hydroxyalkyl)-2H-1,4-diazepin-2-ones include, for example, those of the formula:

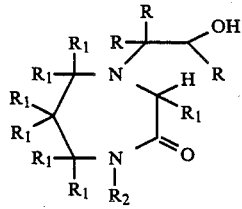

wherein R is either hydrogen or an alkyl group having 1 or 2 carbon atoms, $R_1$ is hydrogen, an alkyl group having 1 to 6 carbon atoms or an aryl or aralkyl group having from 6 to 12 carbon atoms and $R_2$ is hydrogen, an alkyl or hydroxyalkyl having 1 to 6 carbon atoms and aryl or aralkyl having 6 to 12 carbon atoms.

Such hexahydro-4-(hydroxyalkyl)-2H-1,4-diazepin-2-ones include hexahydro-4-(2-hydroxyethyl)2H-1,4-diazepin-2-one, hexahydro-4-(2-hydroxyethyl)-1-methyl-2H-1,4-diazepin-2-one, hexahydro-4-(2-hydroxyethyl)-3-methyl-2H-1,4-diazepin-2-one, hexahydro-4-(2-hydroxyethyl)-5-methyl-2H-1,4-diazepin-2-one, 5-ethyl-hexahydro-4-(2-hydroxyethyl)-2H-1,4-diazepin-2-one, hexahydro-4-(2-hydroxyethyl)-7-methyl-2H-1,4-diazepin-2-one, 7-ethyl-hexahydro-4-(2-hydroxyethyl)-2H-1,4-diazepin-2-one, hexahydro-4-(2-hydroxyethyl)-5,7-dimethyl-2H-1,4-diazepin-2-one, hexahydro-4-(2-hydroxyethyl)-7,7-dimethyl-2H-1,4-diazepin-2-one, hexahydro-4-(2-hydroxyethyl)-7-phenyl-2H-1,4-diazepin-2-one, hexahydro-4-(2-hydroxypropyl)-2H-1,4-diazepin-2-one, hexahydro-4-(2-hydroxybutyl)-2H-1,4-diazepin-2-one, hexahydro-4-(2-hydroxypropyl)-7-methyl-2H-1,4-diazepin-2-one.

Suitable solvents which can be employed in the reaction are water, alcohols, ethers and the like. Particularly suitable solvents include, water, methanol and ethanol, water being preferred. A solvent is not indispensable, but it minimizes the heat of reaction. Usually 20 to 70% of the N-hydroxyalkylalkylenediamine is reacted with 20 to 40% of glyoxal or its substituted derivative in a solvent.

The reaction can be carried out at a temperature between about 0° and about 200° C. Preferably, the reaction is conducted between about 80° and about 100° C. Below 80° C. the product requires long reaction times, otherwise the amount obtained is too small to be of practical value.

The N-hydroxyalkylalkylenediamine and glyoxal, its alkyl-substituted derivative or glyoxal equivalent can be employed in quantities which provide a mole ratio of the diamine to the glyoxal of from about 0.75:1 to about 4:1, preferably from about 1:1 to about 2:1.

The crude reaction product can be purified by vacuum distillation, solvent extraction, recrystallization or any combination of these techniques. Suitable solvents for extraction include aliphatic hydrocarbons, alcohols, esters and chlorinated solvents. Particularly, suitable solvents include hexane, ethanol, isopropanol, ethyl acetate, methylene chloride and chloroform.

The products from the reaction of N-hydroxyalkylalkylenediamines, or their substituted derivative, with glyoxal, its alkyl-substituted derivatives or glyoxal equivalent are useful as hydrochloric acid corrosion inhibitors and adhesion promoters. These products also act as binders between asphalt and fiberglass and between asphalt and rock aggregate, comparing favorably with commercial binder products.

The following examples are representative of the process, its products, their purification and use.

EXAMPLE 1

Into a resin kettle, equipped with a reflux condenser, addition funnel, immersion thermometer, mechanical stirrer and nitrogen purge system, is placed 802 g (7.7 moles) 2-[(2-aminoethyl)amino]ethanol dissolved in 347 g water. The contents in the resin kettle are stirred under nitrogen between 0° and 20° C., using an ice bath. 279 g of 40 wt. % glyoxal in water (1.92 moles) is diluted further with 94 g water and added dropwise to the reactor contents over a period of forty-five minutes. The reactor contents are allowed to stir at ambient temperature for fifteen minutes. Residual 2-[(2-aminoethyl)amino]ethanol and water are removed by vacuum distillation at 250° C. and 10 mm Hg. Infrared spectroscopy supports the presence of 4-(2-hydroxyethyl)-2-piperazinone (4-HEP).

EXAMPLE 2

A 32 wt. % aqueous solution of glyoxal (232 g, 4.0 moles) is added dropwise to a stirred chilled (5° C.) 70 wt. % aqueous solution of 2-[(2-aminoethyl)amino]ethanol (312 g, 3 moles) in a nitrogen atmosphere. The rate of addition of the aqueous solution of glyoxal is controlled so that all the solution is added within 1 hour 42 minutes, with a maximum rise in temperature to 23° C. Twelve days later, the water is removed from the reaction product of glyoxal and 2-[(2-aminoethyl)amino]ethanol by rotary evaporation at 100° C. To insure the removal of all water, isopropanol is added to the reaction product and is removed by rotary evaporation at 100° C. The product from the reaction of glyoxal and 2-[(2-aminoethyl)amino]ethanol is a sticky, black solid. The product is identified by electron impact mass spectroscopy and is shown to be 89% (area) 4-HEP by flame ionization gas chromatography.

EXAMPLE 3

A 30 wt. % aqueous solution of glyoxal (405 g, 7 moles) is added dropwise to a stirred chilled (22° C.) 70 wt. % aqueous solution of 2-[(2-aminoethyl)amino]ethanol (729 g, 7 moles) in a nitrogen atmosphere. The rate of addition of the aqueous solution of glyoxal is controlled so that all the solution is added within 6 hours and 14 minutes with a maximum rise in temperature to 31° C. The reaction product is subjected to rotary evaporation under full vacuum at boiling water temperature. The rotary evaporation bottoms are poured into a feed and degasser flask and subjected to wipedfilm distillation at a temperature between 200° and 255° C. and apressure of 1 mm Hg in a 2"-diameter Pope wiped-film still. A yellowish-brown, viscous liquid is collected in the distillate receiver. This liquid is dissolved in excess 1-propanol and a water-propanol azeotrope removed by fractional distillation at 70° C. at 100 mm Hg. Pressure is reduced to 5 mm Hg and the temperature maintained at 70° C. for 2 hours. The viscous liquid is dissolved in the minimum amount of dry acetonitrile at 60° C.; the flask is capped to exclude water and chilled to 4° C. and held there for 24 to 72 hours. Solids are removed by filtration under a nitrogen pad. White crystals of 4-HEP are obtained when the solids are recrystallized at 50° C. from a minimum amount of acetone. The crystals of 4-HEP melt at 59.5 to 60° C. and boil at 450° C. and are shown to be 99+% pure 4-(2-hydroxyethyl)-2-piperazinone by capillary gas chromatography.

EXAMPLE 4

Preferred method of making a hydroxyalkyl-piperazinone.

A 2 liter resin kettle, equipped with a dropping funnel, thermometer, temperature controller, nitrogen sparge tube, mechanical stirrer, and a chilled water condenser, is charged first with 730 g of deionized water and then 218 g (2.1 moles) of AEEA. Heat was provided by two heat lamps.

There is a mild exotherm due to the heat of solution of AEEA. The stirrer and nitrogen sparge (10 mL/minute) are started and the solution is heated to 100° C. Aqueous glyoxal (20%, 552 grams, 2.00 moles) is added dropwise over three hours. Gas chromatographic analysis shows that the reaction is essentially complete when the glyoxal addition is complete. The heat is removed and 1200 grams of charcoal (NORIT A) is added. The reaction mixture is stirred overnight at ambient temperature, then filtered to remove the charcoal. Gas chromatographic analysis shows 4-HEP to be present in 93% yield.

The following example illustrates a method for preparing one of the new class of amides, specifically hexahydro-4-(2-hydroxyethyl)-2H-1,4-diazepin-2-one.

EXAMPLE 5

A 70 wt. % methanolic solution of 1,3-diaminopropane (715.9 g, 9.7 moles) is added to a resin kettle equipped with a dry ice condenser, immersion thermometer, mechanical stirrer and a sample line consisting of two 3000-lb check valves with 0.5–1 psi cracking pressure and a needle valve. The sample line is connected to a cylinder of ethylene oxide. The ethylene oxide (63.6 g, 1.45 moles) is introduced and reacted at a temperature between 0° and 5° C. The methanol and unreacted 1,3-diaminopropane are removed by rotary evaporation. The yield of 2-[(3-aminopropyl)amino]ethanol (APAE) is 84%.

A 70 wt. % aqueous solution of the above prepared APAE (144.8 g, 1.23 moles) is added to a resin kettle equipped with a reflux condenser, immersion thermometer, mechanical stirrer, addition flask and nitrogen purge system. A 30 wt. % aqueous solution of glyoxal (71 g, 1.23 moles) is added dropwise to the stirred chilled (2° C.) aqueous solution of 2-[(3-amino-propyl)amino]ethanol in a nitrogen atmosphere. The rate of addition is controlled so that all the aqueous solution of glyoxal is added within one hour, with a maximum rise in temperature of 20° C. Water is removed at 100° C. by rotary evaporation. Electron impact and chemical ionization mass spectroscopy and infrared spectroscopy indicates the reaction product to be hexahydro-4-(2-hydroxyethyl)-2H-1,4-diazepin-2-one.

An alternative method of making 4-HEP is to use 2,3-dihydroxy-1,4-dioxane in place of glyoxal. The following example illustrates this method.

EXAMPLE 6

AEEA (0.1 moles) is added to a stirred solution of 2,3-dihydroxy-1,4-dioxane (0.1 mole) in 300 mL of 95% ethanol at 35° C. in a 500 mL Erlenmeyer flask. Potassium carbonate (0.1 mole) was present as catalyst. The solution was heated and stirred at 35° C. for ~6 hours, then allowed to stand overnight at room temperature. gc/ms analysis showed that 4-HEP was present.

The following examples illustrate the utilities of some of the products of the process of the invention.

EXAMPLE 7

Corrosion Inhibition Test

To show a utility for the products of the reaction, the product of Example 2 is tested as a corrosion inhibitor. Two tenths of a percent of 4-(2-hydroxyethyl)-2-piperazinone, a 1010 carbon steel coupon and 100 grams of 10% hydrochloric acid are added to a test tube which is placed in a one-liter Parr bomb and heated for 6 hours at 175°F. The coupon is removed from the bomb, cleaned with 18.5% inhibited HCl, washed and dried. The corrosion rate is calculated according to the following formula:

$$\text{Rate (mpy)} = \frac{534 \times \text{mg. wt. loss of coupon}}{\text{density of coupon} \times \text{surface area of coupon} \times \text{time}}$$

The density is expressed in g/cc, the surface area in sq.in., the time of the test in hrs. and the rate in mils/year (mpy). The percent protection provided by the inhibitor is calculated as follows:

$$\% = \frac{\text{mpy (no inhibitor)} - \text{mpy (with inhibitor)} \times 100}{\text{mpy (no inhibitor)}}$$

The 4-HEP provided 88% protection against acid corrosion. Dowell A-120 and A-250, two commercial inhibitors at the same concentration, exhibit 97 and 99+% protection against acid corrosion, respectively.

EXAMPLE 8

Asphalt Binder Test

Another utility is discovered as a result of the observed adhesive properties of the piperazinones. The Firestone modification of ASTM 2138-H test (cord pullout adhesion) is used to evaluate binders between asphalt and fibre glass. The 4-HEP exhibits better cord pullout adhesion than a control with no binder and slightly better cord pullout than amino silanes available commercially from Union Carbide and Dow Corning. Thus, 4-HEP is a slightly better adhesive for asphalt than the amino silanes.

EXAMPLE 9

Rock Aggregate Anti-strip Test

The 4-HEP exhibits better adhesion than the control and all other compounds tested as asphalt anti-strip agents for rock aggregate. The amino silanes and Ethyleneamine E-100 are among the other compounds tested as asphalt anti-strip agents. In the rock aggregate test, the aggregate is coated with a 5% solution of the anti-strip agent until a 3–5 wt. % pickup is realized. No anti-strip agent is coated on the rock aggregate for the control. Asphalt is applied at five grams per 1000 grams of the binder-coated rock aggregate. The asphalt-coated rock aggregate is heated in an oven for 2 hours at 80° C. and then subjected to boiling water for another hour. The effectiveness of the different anti-strip agents is determined by the observation of several persons. No quantitative data is obtained because of inaccuracies due to some asphalt sticking to the sides of the beaker in the boiling test.

We claim:

1. A process for preparing 4-(2-hydroxyalkyl)-2-piperazinones and their substituted derivatives which comprises: (1) reacting a compound having the formula

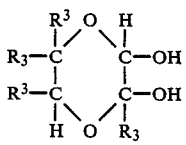

wherein $R_3$ is hydrogen or an alkyl group having from 1–4 carbon atoms, with (2) an N-hydroxyalkylalkylenediamine having the formula

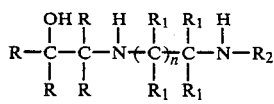

wherein R is hydrogen or an alkyl group of 1 or 2 carbon atoms, $R_1$ is hydrogen, an alkyl group of 1 to 6 carbon atoms, an aryl or an aralkyl group having from 6 to 12 carbon atoms, $R_2$ is hydrogen, an alkyl or hydroxyalkyl group of 1–6 carbon atoms, an aryl or an aralkyl group having from 6 to 12 carbon atoms and n is 1 or 2.

2. The process of claim 1 wherein R, $R_1$ and $R_2$ are each hydrogen.

3. The process of claim 2 wherein n is 1.

4. The process of claim 2 wherein n is 2.

5. The process of claim 1 wherein the ratio of the reactant amine to the [$\alpha,\beta$-dicarbonyl compound] 2,3-dihydroxy-1,4-dioxane, or its alkyl derivative, is from about 0.75/1 to about 4/1.

6. The process of claim 5 wherein the ratio is from about 1/1 to about 2/1.

7. The process of claim 1 wherein the reaction is conducted at a temperature within the range of from about 0° to about 200° C.

8. The process of claim 7 wherein the temperature is within the range of from about 80° to about 100° C.

9. The process of claim 1 wherein R and $R_1$ each is hydrogen.

10. The process of claim 9 wherein $R_2$ is alkyl.

11. The process of claim 10 wherein the alkyl group is methyl or ethyl.

12. The process of claim 9 wherein $R_2$ is hydroxyalkyl.

13. The process of claim 9 wherein the hydroxyalkyl group is hydroxyethyl.

14. The process of claim 1 wherein R and $R_2$ each is hydrogen.

15. The process of claim 14 wherein at least one $R_1$ is alkyl.

16. The process of claim 15 wherein the alkyl group is methyl or ethyl.

* * * * *